United States Patent [19]

Davidson et al.

[11] Patent Number: 5,168,655
[45] Date of Patent: Dec. 8, 1992

[54] HYDROPONIC CROP PRODUCTION

[75] Inventors: Andrew A. Davidson, Bristol, England; Robert A. K. Szmidt, Ayr, Scotland

[73] Assignee: Albright & Wilson Limited, Warley, Great Britain

[21] Appl. No.: 864,169

[22] Filed: Apr. 3, 1992

Related U.S. Application Data

[63] Continuation of Ser. No. 739,774, Jul. 30, 1991, abandoned, which is a continuation of Ser. No. 414,127, Sep. 29, 1989, abandoned.

[30] Foreign Application Priority Data

Sep. 29, 1988 [GB] United Kingdom ............... 8822908

[51] Int. Cl.$^5$ .............................................. A01G 31/00
[52] U.S. Cl. ...................................................... 47/62

[56] References Cited

U.S. PATENT DOCUMENTS

| | | | |
|---|---|---|---|
| 3,705,467 | 12/1972 | McKnight | 47/9 |
| 4,221,660 | 9/1980 | Eggensperger | 252/186.42 |
| 4,354,327 | 10/1982 | Smeltzer | 47/58 |
| 4,804,530 | 2/1989 | Sampathkumar | 514/557 |
| 4,824,591 | 4/1989 | Dyroff | 252/186.23 |
| 4,917,811 | 4/1990 | Foster | 252/186.23 |

FOREIGN PATENT DOCUMENTS

| | | |
|---|---|---|
| 0035800 | 9/1981 | European Pat. Off. |
| 8802806 | 1/1990 | Netherlands |
| 2152377 | 8/1985 | United Kingdom |
| 2187958 | 9/1987 | United Kingdom |

OTHER PUBLICATIONS

Hydroponic Food Production by Resh SB126.5 R47 ©1981 pp. 88, 89, 160, 161, 176, 177.

Primary Examiner—David A. Scherbel
Assistant Examiner—Michele A. Van Patten
Attorney, Agent, or Firm—Frishauf, Holtz, Goodman & Woodward

[57] ABSTRACT

Hydroponic substrates are disinfected in situ, prior to a crop production cycle, with a dilute aqueous solution containing hydrogen peroxide and at least one peracid having a

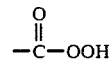

group.

25 Claims, No Drawings

HYDROPONIC CROP PRODUCTION

This application is a continuation of application Ser. No. 07/739,774, filed Jul. 30, 1991 (abandoned), which is a continuation of application Ser. No. 07/414,127, filed Sep. 29, 1989 (abandoned).

This invention relates to hydroponic crop production.

Horticulture and agriculture increasingly rely on advanced production technology to maintain their competitiveness. The use of hydroponic crop production methods has led to the production of high quality crops at high yields. The crops so produced include tomatoes and cucumbers.

Hydroponic crop production normally involves the use of a substrate, for example of rockwool or perlite, on which the crop is grown. Some methods do not involve the use of a substrate however and rely on a thin film of nutrient liquid being guided by a trough or other conduit to flow over the plant roots and provide nutrition for the plant.

In both the production methods which involve substrates and those which do not, it is important that the substrate or fluid conduit is free at the beginning of each production cycle from any residues or contaminants harmful to the plants to be grown. This necessity has led to hydroponic substrates being discarded after a single growing cycle, with the resultant considerable wastage of materials, or to the substrates being removed from the locations they occupy during crop production to be sterilised by, for example, steam treatment or microwave or radio-frequency radiation treatment. All these treatments involve handling and transportation of the substrates and are energy- and labour-intensive. As an alternative, treatment of the substrates with a fungicide or soil sterilant might be considered. These materials are however themselves subject to considerable disadvantages: fungicides, which usually produce undesirable residues in effluent wash water, are moreover usually specific in their action (and would therefore not be effective against a wide range of contaminants unless a large number of fungicides were used simultaneously); soil sterilants such as methyl bromide (a toxic gas requiring careful, specialist handling) usually leave behind toxic residues which would render the substrate unsuitable for further use. Corresponding disadvantages arise when it is desired to remove harmful residues from the hydroponic fluid conduits used in hydroponic production not involving a substrate.

It has now been found that when a hydroponic substrate is treated after use with sufficient of a percarboxylic acid to reduce the microbial population without totally sterilising the medium, improved plant growth is obtained in a subsequent growth cycle compared even with the fresh medium. This surprising result is apparently due to the ability of benign microflora to recolonise the substrate after percarboxylic acid treatment, and the absence of toxic residues from the percarboxylic acid itself.

The result is particularly surprising since percarboxylic acids have not been found very satisfactory as soil sterilants. It is believed that this may be due to the relatively high concentration of organic matter in soil which may inactivate percarboxylic acid at all but very high levels thereof. Hydroponic substrates are generally characterised by relatively low organic contents, typically less than 5% by volume e.g. less than 3% preferably less than 2% less than 1% or less than 0.5% by volume.

The present invention accordingly provides a method of hydroponic crop production in which a hydroponic substrate and/or the liquid-supply means of a hydroponic system which has been infected with a microbial population is treated after a crop-production cycle and prior to a subsequent crop-production cycle with sufficient of a dilute aqueous solution containing at least one peracid having a

group substantially to reduce but not eliminate the microbial population. Preferably the dilute aqueous solutions also contain hydrogen peroxide.

With such a method, in situ disinfection of the hydroponic substrate or liquid-supply means can be readily carried out and the need for time- and energy-consuming removal and transportation of the substrate avoided. The dilute treatment solution can be conveniently supplied to the substrate through the same irrigation system as is used for supply of liquid nutrients to the plants during the growing cycle. Any trace of peracid remaining after treatment can be removed by flushing through the same irrigation system. In any event, the use of a peracid as mentioned above, for example peracetic acid, will normally produce no harmful residue because of its breakdown to the corresponding acid, for example acetic acid, and hydrogen peroxide which itself decomposes to water and oxygen. Disinfection of the substrate is achieved, giving a significant reduction in the microbial population but leaving a residual community and a dynamic environment in which recolonisation may readily occur. Recolonisation with a low level of microorganisms is believed to promote higher plant growth yields. In particular, a balanced microbial population inhibits the growth of any pathogens that may reinfect the medium. Moreover, with treatment processes according to the invention, no phytotoxic effects have been observed. Treatment according to the invention can be carried out quickly, with consequent reduction of the downtime of the hydroponic system, and is effective against a broad spectrum of contaminants. Furthermore, no deterioration in the hydroponic substrate as a result of treatment according to the invention has been observed.

The peracid used is preferably a percarboxylic acid, more preferably peracetic or perpropionic acid.

The treatment solution will usually be prepared by dilution of a more concentrated solution of the peracid. Such solutions of the peracid may be unstable on prolonged storage and the treatment solution will preferably be analysed prior to the treatment process in order to establish the concentration of the peracid in the treatment solution.

The solutions will thereby preferably not contain any additional ingredient which may tend to destabilise the peracid. In particular, the presence of significant quantities of dissolved salts is to be avoided.

The concentrates may contain a wetting agent. A preferred group of wetting agents is those which exhibit some bactericidal activity, the most preferred wetting agent being aromatic alkyl and especially benzene sulphonic acids. Examples of such acids are the alkyl aryl sulphonic acids which have from 6 to 18 carbon atoms in the alkyl substituent of the molecule, especially those which have from 9 to 15 carbon atoms in the alkyl substituent. The sulphonic acid may take the form of a mixture of alkyl aryl sulphonic acids wherein the number of carbon atoms in the alkyl substituent varies but has an average value of from 6 to 18 carbon atoms. Examples of alkyl aryl sulphonic acids which are useful include acids derived from aromatic nuclei other than benzene, such as toluene and xylene, as well as those derived from benzene itself. Examples of useful sulphonic acids include decyl toluene, dodecyl xylene, octyl benzene, nonyl benzene, decyl benzene, tridecyl benzene, tetradecyl benzene, pentadecyl benzene, dodecyl benzene and hexadecyl benzene sulphonic acids. The preferred sulphonic acid is dodecyl benzene sulphonic acid. The concentrates may also comprise any of the conventional stabilisers for percarboxylic acids such as 2,6 pyridine dicarboxylic acid and phytic acid.

The concentrates may be produced by mixing the components thereof in any order. The peracid may be added as a solution thereof or may be generated in situ by the reaction of hydrogen peroxide with the corresponding acid or acid anhydride. The product of these mixing procedures is an aqueous solution comprising hydrogen peroxide, peracid and acid in dynamic equilibrium. The rate of reaction between hydrogen peroxide and the acid is usually relatively slow at ambient temperatures and the mixture may not reach equilibrium for a considerable period in some circumstances. These processes represent the preferred method for the production of the concentrates and the conditions under which the mixing of the appropriate quantities of peroxide and the acid or peracid is carried out may be adjusted to ensure that a predetermined minimum concentration of peracid is produced.

The preferred concentrates for use in this invention contain from 0.5 to 20%, preferably from 1.0 to 10.0% and more preferably from 2.0 to 7.0% by weight of peracid and from 10 to 50%, preferably 10 to 35%, and most preferably 15 to 25% by weight of hydrogen peroxide, the ratio of the weight of hydrogen peroxide to peracid preferably being in the range 2:1 to 10:1, more preferably in the range 4:1 to 7:1. In general the stability of the concentrates increases as the concentration of the peracid increases and should be at least 3.0% by weight and more preferably at least 3.5% by weight of the concentrate. Any hydroponic substrate, including rockwool, perlite, silica, gels and plastics foam substrates, may be treated in accordance with the invention, as may all troughs and other conduits used. Substrates high in organic matter, for example soil and peat, cause breakdown of the concentrates. Preferably, the substrates to be treated in the present invention contain less than 2% by volume of organic matter when first used. Crop residues derived from plant growth do not inactivate the concentrates.

The stability of the concentrates decreases as the amount of water present increases. The amount of water present in the concentrates is preferably in the range 40 to 75% by weight and more preferably in the range 50 to 70%. The ratio of the amount of water to the amount of peracid (at equilibrium) is preferably in the range 10:1 to 20:1, more preferably in the range 12:1 to 18:1. The maximum concentration of peracid is preferably not greater than 7.0% and more preferably not greater than 5.0% by weight because greater concentrations of peracid present difficulties in transporting and handling the concentrate. Where the peracid is to be generated in situ by the reaction of hydrogen peroxide with the corresponding acid or acid anhydride, the quantity of hydrogen peroxide which is used will be adjusted so as to take into account the quantity of hydrogen peroxide which is liable to be consumed in this reaction.

A concentrate containing peracid is preferably produced by adding glacial acetic acid to a solution of hydrogen peroxide. The formulation of peracetic acid may be accelerated by the addition of a catalytic quantity of a mineral acid, but this is less preferred since it adds to the corrosive nature of the product. Alternatively the concentrate can be produced by the addition of hydrogen peroxide solution to commercially available peracetic acid products.

The concentrates mentioned may be used at dilution rates of, say, 25, 50, 75, 100 or 200 v/v. The concentration of peracid in the treatment solution being preferably from 0.001 to 0.05 mol dm$^{-3}$, more preferably from 0.0025 to 0.02 mol dm$^{-3}$ and most preferably from 0.005 to 0.01 mol dm$^{-3}$.

The application rate of treatment solution to hydroponic substrate is preferably 0.1:1 to 5.0:1 v/v (i.e., from one-tenth to five volumes of treatment solution applied per volume of substrate), more preferably from 0.5:1 to 1.0:1 and most preferably from 0.66:1 to 0.83:1.

The present invention is applicable equally to hydroponic substrates used for the production of any crop, including edible crops, such as tomatoes and cucumbers, ornamental plants and flowers for cutting.

The invention will now be described further with reference to the following example and test results.

EXAMPLE 1

An aqueous concentrate comprising peracetic acid was made by mixing the following ingredients.

|  | Percent m/m |
| --- | --- |
| Acetic acid | 10.3 |
| Hydrogen peroxide (35% solution) | 70.9 |
| 2,6-pyridine dicarboxylic acid | 0.015 |
| Dodecyl benzene sulphonic acid | 1.2 |
| Water | 17.585 |

The composition (composition "A") was mixed, left to stand at 50° C. for 19 hours, cooled to ambient temperature and sampled prior to use to determine the peracetic content.

TEST RESULTS

A range of hydroponics substrate samples was treated with diluted composition A and assayed for populations of bacteria and fungi. Controls were of untreated material.

Four substrate samples were used:
(1) Rockwool (Grodania A/S) previously used for cucumber production.
(2) New rockwool (Grodania A/S).
(3) Horticultural grade perlite (Tilcon Ltd) previously used for tomato production.
(4) New horticultural grade perlite (Tilcon Ltd).

Composition A was diluted at 1:50 and 1:100 v/v and the diluted solution applied to the substrate at a rate of 0.66 to 0.83:1 v/v (20 to 25 dm$^3$ solution applied to 30 dm$^3$ of substrate). Variable grading and settlement of materials, in particular perlite, preclude accurate determination of volume.

The substrate samples were assayed as follows. Samples of approximately 30 dm$^3$ of each substrate were treated with a dilute solution of composition A and with equivalent volumes of clean mains water. Representative sub-samples, each weighing 5 g, were ground in 15 cm$^3$ sterile distilled water and 0.1 cm$^3$ of serial dilutions plated onto each of two plates of Czapex-Dox plus yeast extract agar (CD+ye). CD+ye is a specific medium, pH 4, for promoting growth of fungi. In addition, two plates containing Nutrient agar (NA) were inoculated with sub-samples from each serial dilution. The plates were incubated for 3 days at 20° C. prior to counting of bacterial colonies on NA, and for 4 days at 20° C. prior to counting of fungal colonies on CD+ye. The moisture contents of the substrate samples were determined and results expressed as colony forming units (cfus) or bacteria per gram (dr wt).

Application of composition A to both used and new rockwool and perlite at a dilution of 1:50 eliminated all fungal and bacterial populations. Reference should now be made to Table 1.

TABLE 1

Fungal and bacterial populations in rockwool and perlite treated or untreated with composition A (g$^{-1}$ dr wt)

| Treatment/sample | Fungal cfus | Bacteria |
|---|---|---|
| Composition A @ 1:50 | | |
| Used rockwool | 0 | 0 |
| | 0 | 0 |
| New rockwool | 0 | 0 |
| | 0 | 0 |
| Used perlite | 0 | 0 |
| | 0 | 0 |
| New perlite | 0 | 0 |
| | 0 | 0 |
| Water controls | | |
| Used rockwool | $2.0 \times 10^5$ | $2.6 \times 10^5$ |
| | $3.8 \times 10^5$ | $2.6 \times 10^5$ |
| New rockwool | $1.2 \times 10^2$ | $3.5 \times 10^7$ |
| | $1.2 \times 10^2$ | $1.4 \times 10^7$ |
| Used perlite | 0 | $2.7 \times 10^6$ |
| | 0 | $4.7 \times 10^6$ |
| New perlite | $1.7 \times 10^2$ | $1.1 \times 10^7$ |
| | $1.7 \times 10^2$ | $6.9 \times 10^6$ |

Growing and phytotoxicity trials were carried out to identify the level of phytotoxicity of composition A when used as a pre-planting drench to once-used hydroponic substrates. Phytotoxicity was tested using rapid bioassay techniques. The use of treated material for the production of salad crops was then investigated.

In order to determine the presence or absence of any phytotoxic residues in hydroponic substrates previously treated with composition A, a rapid assay method based on standard procedures was adopted. The assay method for Dazomet soil residue determination using cress germination and growth (BASF UK Ltd) was utilised.

Rockwool and perlite samples were treated with composition A at a dilution of 1:50 or 1:100, or with clean water. Test solutions were applied to approximately 0.5 dm$^3$ samples of used rockwool (Grodania A/S). Samples of a similar volume of used perlite (Tilcon Ltd) were also used.

Assessment of phytotoxicity was carried out by treating substrate samples with composition A and subsequently flushing twice, to run off, with clean water prior to bioassay.

Substrate samples were treated with composition A solutions or water controls and allowed to soak for one hour. The samples were then drained overnight and placed in plastic trays in a glasshouse before being surface-seeded with cress and maintained in the glasshouse with a heating thermostat setpoint of 18° C. and a ventilation setpoint 24° C. Germination and subsequent growth were assessed on a subjective scale of 0 to 5. (0=no germination or seedling death; 5=good germination and growth). The samples were kept moist with nutrient solution as required. The results obtained showed that germination was good in all cases.

TABLE 2

Mean growth score for cress sown onto flushed rockwool and perlite previously treated with composition A

| Treatment/sample | 0 = poor; 5 = good Mean growth score after 6 days |
|---|---|
| Composition A @ 1:100 | |
| Used rockwool | 4 |
| Used perlite | 4.5 |
| Composition A @ 1:50 | |
| Used rockwool | 4 |
| Used perlite | 4.5 |
| Water controls | |
| Used rockwool | 5 |
| Used perlite | 5 |

On the basis of results from rapid bioassay of compound A residues and efficacy data indicating activity of product against natural populations of bacteria and fungi, compound A was tested on crop plants. Tomatoes were grown in treated and untreated perlite and cucumbers grown in treated and untreated rockwool and maintained under standard commercial conditions prior to assessment of plant establishment and growth.

Materials and methods

Substrate and crop combinations:
  i) Cucumber grown in rockwool.
  ii) Tomato grown in perlite.
Substrates:
  i) Rockwool
    Propagation: New cubes (Capogro Ltd) approximately 7 cm×7 cm×7 cm.
    Growing on: Once-used slabs (Grodania A/S) (Glass Glover Ltd) approximately 90 cm×27 cm×6 cm.
  ii) Perlite (Tilcon Ltd)
    Propagation: New perlite in 13 cm mesh based pots (Plantpak Ltd).
    Growing on: Once-used perlite (Tilcon Ltd) 25 dm$^3$ growing modules.
Crop species:
  i) Cucumber cv Tinda (Enza Zaden BV).
  ii) Tomato cv 663 RZ F1 (Rijk Zwaan BV).

'Planting' was carried out using current commercial practices over a six-day period. Cucumbers were 'planted' by placing young plants directly onto growing slab surfaces. Tomato plants were 'planted' by partial plunging of the propagation pot into the top 2 to 3 cm of the perlite growing modules.

Each 25 dm$^3$ perlite growing module was planted with three tomato plants. The modules were positioned end to end in rows within a glasshouse. Each rockwool slab was planted with two cucumber plants. The modules were positioned end-to-end in rows within a glasshouse. Both species were trained up vertical strings and side shoots removed at an early stage to maintain a single plant stem in each case. Irrigation water and nutrients were applied manually on a twice-daily basis, or more frequently as required under bright conditions. Nutrition was supplied according to current recommendations. Environmental control was provided by a Van Vliet CR-12 environmental computer. The heating thermostat setpoint was 18° C. with a ventilation set point of 24° C. The plants were destructively harvested five weeks after planting and assessed for establishment and growth in the various treated substrates.

The plants were visually assessed for plant establishment and root and shoot development after 5 weeks growth under standard commercial conditions. Within the course of the trial, plant growth was sufficiently good to ensure flower set and fruit development in all treatments. This formed the basis of records of plant productivity in view of the commercial relevance of fruit, rather than foliage, production.

All tomato and cucumber plants established well both in untreated perlite and rockwool and in material previously treated with compound A and flushed out with water prior to planting. All plants scored on the basis of a subjective scale (1=poor; 5=good) scored 5 for both root production and healthy foliage production. No evidence of root death or scorching of foliage was noted for any treatment. Differences between treated plots and untreated controls (Tables 3 and 4) were slight in all cases. No evidence of phytotoxic residues in either rockwool or perlite was detected.

TABLE 3

Plant growth and fruit development of cucumbers grown in substrate treated or untreated with composition A (mean of 6 plants)

| Crop | Height (cm) | No. of fruit | Fruit wt. (g) | Total fresh weight (g) |
| --- | --- | --- | --- | --- |
| Cucumber (i) | | | | |
| Rockwool treated with composition A @ 1:50 | 112.17 | 1 | 14.80 | 519.86 |
| S.E.M. (standard error of mean) | 2.06 | 0 | 2.53 | 7.96 |
| Cucumber (i) | | | | |
| Rockwool untreated control | 115.33 | 1.17 | 13.50 | 538.74 |
| S.E.M. | 6.31 | 0.41 | 8.56 | 61.40 |
| Cucumber (ii) | | | | |
| Rockwool treated with composition A @ 1:50 | 139.83 | 6.00 | 1208.20 | 1610.80 |
| S.E.M. | 13.60 | 0.89 | 254.00 | 266.00 |
| Cucumber (ii) | | | | |
| Rockwool untreated control | 158.20 | 6.40 | 1467.80 | 2003.50 |
| S.E.M. | 21.50 | 0.55 | 703.00 | 773.00 |

TABLE 4

Plant growth and development of tomatoes grown in substrate treated or untreated with composition A (mean of 12 plants)

| Crop | Height (cm) | No. of fruit (Truss No) | Fruit wt. (g) | Total fresh weight (g) |
| --- | --- | --- | --- | --- |
| Tomato | | | | |
| Perlite composition A @ 1:100 | 130.50 | 22.50 (3.75) | 124.29 | 602.12 |
| S.E.M. | 1.66 | 1.17 (0.13) | 7.56 | 10.47 |
| Tomato | | | | |
| Perlite untreated controls | 124.50 | 20.25 (3.17) | 137.49 | 595.14 |
| S.E.M. | 3.29 | 0.91 (0.16) | 9.87 | 18.60 |

Composition A at a dilution of 1:50 or 1:100 may also be used to prepare the liquid-supply troughs of a no-substrate hydroponics system for a fresh crop production cycle. The composition can be supplied through the irrigation system normally used for the nutrient liquid, the irrigation system and liquid supply troughs being thoroughly flushed afterwards with clean water.

EXAMPLE 2

Laboratory scale investigations were performed to investigate the effect of sample preparation on recovery of micro-organisms from treated and untreated perlite and the influence of organic matter on the effectiveness of composition A as a sterilant.

Method

1. Six or eight flasks were inoculated with 100 g perlite to which 3 or 4 had 66 $cm^3$ water added and 3 or 4 had 66 $cm^3$ of 1:100 composition A.
2. Flasks were shaken to mix the sample and were then incubated statically for 24 hours at 30° C.
3. The samples were then removed, the composition A inactivated, by either filter washing or sodium thiosulphate, and microbial counts performed.

Two procedures for inactivating composition A were tested. The first was the filter wash where composition B was diluted and then removed by washing the perlite with water, trapping bacteria in the wash water on a membrane filter, followed by homogenisation of both the perlite and the filters.

The other procedure was chemical inactivation with sodium thiosulphate.

There was no significant differences between the counts obtained using either method and it was concluded that sodium thiosulphate is a satisfactory inactivator to use in this application.

The first laboratory scale test using perlite taken from recently used bags in-situ in the greenhouse gave a 2.5 log reduction in bacterial counts and approximately 2 log reductions in yeast and fungal counts. There was some peaty organic matter in the perlite and laboratory trails were carried out to determine the impact of this organic material on the effectiveness of composition A.

Two samples of perlite were compared. A stored used perlite, low in organic matter provided the low organic matter samples. High organic matter perlite was prepared by the addition of the peaty residues of propagation pot compost, which were obtained from used perlite bags.

In the low organic matter perlite the bacterial counts were reduced by 4.5 logs while bacterial spore counts, yeasts and moulds were reduced by around 2 logs. The presence of the peaty material almost completely inactivated composition A. There was no significant reduction in bacterial or yeast numbers and there was only a 30 to 50% reduction in the numbers of bacterial spores and moulds.

Reference should now be made to Tables 5 and 6.

TABLE 5

Counts per gram dry weight of treated and untreated low organic content perlite (lab scale)
N.B. Counts are exponents, i.e. 2.74 10E7 = 2.74 × $10^7$

| Treatment | Time | Bacteria | Spores | Yeast | Moulds |
|---|---|---|---|---|---|
| A | X | 2.74 10E7 | 1.08 10E4 | 1.22 10E5 | 9.46 10E4 |
| A | X | 1.57 10E7 | 1.04 10E4 | 4.05 10E4 | 8.11 10E4 |
| A | X | 1.84 10E7 | 1.19 10E4 | 2.0 10E4 | 6.76 10E4 |
| B | X | 1.57 10E7 | 8.78 10E3 | 2.0 10E4 | 2.7 10E4 |
| B | X | 2.19 10E7 | 1.36 10E4 | 4.05 10E4 | 8.11 10E4 |
| B | X | 2.38 10E7 | 1.84 10E4 | 2.0 10E4 | 5.4 10E4 |
| C | X | 2.0 10E2 | 2.0 10E2 | 2.0 10E1 | 2.0 10E2* |
| C | X | 2.0 10E2 | 2.0 10E2 | 2.0 10E2 | 2.0 10E2* |
| C | X | 2.0 10E2 | 2.0 10E2 | 2.0 10E2 | 2.0 10E2* |
| D | X | 2.0 10E2 | 2.0 10E2 | 2.0 10E2 | 2.0 10E2* |
| D | X | 4.05 10E2 | 2.0 10E2 | 2.0 10E2 | 2.0 10E2* |
| D | X | 1.62 10E3 | 2.0 10E2 | 2.0 10E2 | 2.0 10E2* |
| A | Y | 9.86 10E6 | 1.32 10E4 | 2.0 10E4 | 2.0 10E4* |
| A | Y | 1.42 10E7 | 2.76 10E4 | 2.0 10E4 | 2.0 10E4* |
| A | Y | 1.40 10E7 | 8.65 10E3 | 1.22 10E4 | 8.11 10E3 |
| B | Y | 1.00 10E7 | 2.85 10E4 | 2.0 10E4 | 2.0 10E4* |
| B | Y | 1.70 10E7 | 1.00 10E4 | 2.0 10E4 | 2.70 10E4 |
| B | Y | 8.65 10E6 | 7.43 10E4 | 1.22 10E4 | 1.08 10E4 |
| C | Y | 2.0 10E2 | 2.7 10E2 | 4.05 10E2 | 4.05 10E2 |
| C | Y | 2.0 10E2 | 5.4 10E2 | 2.0 10E2 | 2.0 10E2* |
| C | Y | 2.0 10E2 | 2.0 10E2 | 2.0 10E2 | 2.0 10E2* |
| D | Y | 0.0 10E0 | 5.40 10E2 | 2.0 10E3 | 3.51 10E3 |
| D | Y | 4.05 10E2 | 2.0 10E2 | 2.0 10E2 | 2.0 10E2* |
| D | Y | 2.0 10E2 | 2.0 10E2 | 2.0 10E2 | 2.0 10E2* |

Key:
Treatment:
A = Before application and filter wash
B = Before application and thiosulphate inactivation
C = After filter wash
D = After thiosulphate
Time:
X = After 24 hours treatment
Y = After 48 hours treatment
*Inaccurate due to plate overgrowth

TABLE 6

Counts per gram dry weight of treated and untreated high organic content perlite (lab scale)
N.B. Counts are exponents, i.e. 1.61 10E8 = 1.61 × $10^8$

| Treatment | Bacteria | Spores | Yeast | Moulds |
|---|---|---|---|---|
| A | 1.61 10E8 | 4.05 10E6 | 8.95 10E5 | 2.04 10E6 |
| A | 1.94 10E8 | 5.38 10E6 | 1.31 10E6 | 4.20 10E6 |
| A | 1.30 10E8 | 5.04 10E6 | 7.82 10E5 | 2.87 10E6 |
| B | 1.33 10E8 | 3.28 10E6 | 1.02 10E6 | 1.91 10E6 |
| B | 2.21 10E8 | 3.15 10E6 | 1.18 10E6 | 3.28 10E6 |
| B | 1.25 10E8 | 4.52 10E6 | 7.82 10E5 | 3.26 10E6 |
| C | 1.31 10E8 | 1.67 10E6 | 1.09 10E6 | 7.71 10E5 |
| C | 1.06 10E8 | 1.95 10E6 | 1.17 10E6 | 8.71 10E5 |
| C | 1.35 10E8 | 1.46 10E6 | 9.37 10E5 | 8.86 10E5 |
| D | 1.26 10E8 | 1.52 10E6 | 1.29 10E6 | 1.08 10E6 |
| D | 1.15 10E8 | 1.38 10E6 | 1.34 10E6 | 8.96 10E5 |
| D | 1.42 10E8 | 1.26 10E6 | 8.86 10E5 | 7.59 10E5 |

Key: Treatment
A = Before application and filter wash
B = Before application and thiosulphate inactivation
C = After filter wash
D = After thiosulphate

In vivo application

Perlite, separate from that used for crop production, was treated with composition A and assessed for microbiological 'kill'. This was carried out according to the following schedule.
1. One or two plastic 'tubes' containing ten perlite bags were chosen for sampling.
2. The 10 perlite bags were labelled as appropriate.
3. Each perlite bag contained 3 inlets for composition A, which were sampled.
4. The samples were removed from the whole depth of each inlet using a scoop sterilised with alcohol between samples. Samples remote from the inlet were taken by cutting the plastic bag and sampling to approximately 10 cm depth.
5. Once sampled, the hole left by sampling was caved in using adjacent perlite.
6. Samples were put into stomacher bags and transferred to the lab for testing.

N.B. The method of sampling was randomised using 10 petri dishes with 3 labels in each, i.e. left, right and middle. A label was chosen from each dish in turn, so as to create a sampling plan.

No attempt was made to remove any peat, algae, roots etc, which were present in the samples.

Two series of tests were run using perlite.

In test series 1, the perlite around the inlets was contaminated with peaty material derived, presumably, from the rooting compost in which the plants were grown before planting out. The perlite in test series 2 was free from such extraneous material. Perlite bags were tested in the glass house before and directly after treatment with composition A.

TEST SERIES 1

The composition A reduced the bacterial count by 2.5 log, roughly 300-fold. After one week the numbers of bacteria had recovered to about 30% of the original count. Immediately after treatment yeast numbers were only reduced by 1.2 logs, about 15-fold, and the moulds by only 0.7 logs, or about 5-fold. Numbers of yeasts recovered to their original level after 1 week but mould numbers did not increase.

TEST SERIES 2

There was roughly a 3 log reduction in bacterial counts. The bacterial spore count was reduced by only 1.2 logs while the yeasts and moulds were reduced by 2 logs. The bacterial counts recovered after 1 week while the small increases in spore and mould numbers were not statistically significant.

There is a greater reduction in microbial counts in series 2 compared to series 1. This confirms the laboratory scale findings that composition A is more effective in disinfecting perlite containing no peat compost around the planting sites.

Reference should be made to Tables 7 and 8.

TABLE 7

Series 1
Counts per gram dry weight of perlite before, during and after treatment.
N.B. Counts are exponents, i.e. 3.31 10E8 = 3.31 × $10^8$

| Point | Type (a) | Bacteria | Yeast | Moulds |
|---|---|---|---|---|
| 1 | A | 3.31 10E8 | 1.58 10E5 | 4.74 10E6 |
| 2 | A | 6.23 10E8 | 7.62 10E6 | 1.63 10E7 |
| 3 | A | 4.03 10E8 | 1.65 10E4 | 1.58 10E7 |
| 4 | A | 1.21 10E9 | 3.27 10E4 | 5.81 10E5 |
| 5 | A | 5.55 10E8 | 2.67 10E9 | 3.75 10E7 |
| 6 | A | 9.97 10E8 | 1.68 10E6 | 1.68 10E6 |
| 7 | A | 7.35 10E8 | 1.7 10E6 | 9.62 10E6 |
| 8 | A | 1.29 10E8 | 1.18 10E6 | 2.24 10E6 |
| 9 | A | 2.5 10E8 | 6.13 10E5 | 1.66 10E6 |
| 10 | A | 2.97 10E8 | 1.51 10E6 | 1.92 10E6 |
| 11 | B | 3.42 10E6 | 4.69 10E5 | 1.78 10E5 |
| 12 | B | 2.46 10E6 | 1.64 10E5 | 1.38 10E6 |
| 13 | B | 1.08 10E6 | 6.68 10E5 | 4.01 10E6 |

TABLE 7-continued

Series 1
Counts per gram dry weight of perlite before, during
and after treatment.
N.B. Counts are exponents,
i.e. 3.31 10E8 = 3.31 × $10^8$

| Point | Type (a) | Bacteria | Yeast | Moulds |
|---|---|---|---|---|
| 14 | B | 2.79 10E6 | 1.72 10E5 | 3.21 10E7 |
| 15 | B | 1.81 10E5 | 4.29 10E6 | 9.15 10E6 |
| 16 | B | 3.57 10E6 | 1.6 10E4 | 2.17 10E5 |
| 17 | B | 9.40 10E5 | 6.42 10E3 | 4.28 10E4 |
| 18 | B | 5.39 10E4 | 1.88 10E3 | 2.92 10E5 |
| 19 | B | 1.07 10E6 | 4.63 10E4 | 8.91 10E5 |
| 20 | B | 1.43 10E6 | 1.05 10E4 | 2.02 10E5 |
| 21 | C | 9.39 10E7 | 8.36 10E5 | 1.91 10E6 |
| 22 | C | 2.96 10E8 | 1.44 10E6 | 8.21 10E5 |
| 23 | C | 1.19 10E8 | 1.38 10E6 | 1.36 10E6 |
| 24 | C | 4.06 10E8 | 9.30 10E5 | 3.97 10E6 |
| 25 | C | 2.84 10E8 | 4.20 10E6 | 1.09 10E6 |
| 26 | C | 2.81 10E7 | 5.83 10E5 | 9.87 10E5 |
| 27 | C | 7.17 10E7 | 1.62 10E6 | 1.90 10E5 |
| 28 | C | 4.88 10E6 | 1.39 10E5 | 1.50 10E5 |
| 29 | C | 1.71 10E8 | 6.72 10E6 | 2.56 10E6 |
| 30 | C | 4.14 10E8 | 6.64 10E5 | 6.35 10E5 |

Key: (a)
A = Before treatment
B = Immediately after application
C = After flushing

TABLE 8

Series 2
Counts per gram dry weight in treated and untreated
low organic content perlite in a glasshouse.
N.B. Counts are exponents,
i.e. 5.08 10E7 = 5.08 × $10^7$

| Treatment | Type | Bacteria | Spore | Yeast | Moulds |
|---|---|---|---|---|---|
| A | X | 5.08 10E7 | 4.41 10E4 | 1.17 10E6 | 3.0 10E7* |
| A | Y | 7.80 10E7 | 2.15 10E4 | 2.43 10E6 | 2.43 10E5 |
| A | X | 9.18 10E7 | 9.23 10E4 | 2.18 10E5 | 1.30 10E6 |
| A | Y | 7.85 10E7 | 2.00 10E5 | 4.45 10E5 | 5.0 10E7* |
| A | X | 1.38 10E7 | 8.65 10E6 | 1.65 10E7 | 1.41 10E7 |
| A | Y | 2.38 10E8 | 1.83 10E5 | 4.46 10E6 | 1.15 10E6 |
| A | X | 1.50 10E8 | 5.35 10E4 | 7.45 10E5 | 4.00 10E7* |
| A | Y | 7.57 10E7 | 7.35 10E4 | 7.00 10E4 | 4.00 10E7* |
| A | X | 7.61 10E7 | 1.31 10E5 | 1.20 10E6 | 2.00 10E7* |
| A | Y | 1.54 10E8 | 1.83 10E4 | 6.24 10E4 | 1.25 10E5 |
| A | X | 1.32 10E7 | 6.27 10E4 | 9.00 10E4 | 1.91 10E5 |
| A | Y | 6.36 10E7 | 4.57 10E4 | 8.00 10E4 | 2.24 10E5 |
| A | X | 8.02 10E7 | 1.50 10E5 | 8.58 10E5 | 2.20 10E7* |
| A | Y | 2.11 10E7 | 3.76 10E4 | 9.01 10E5 | 5.00 10E5 |
| A | X | 6.87 10E7 | 1.80 10E5 | 2.43 10E6 | 9.59 10E5 |
| A | Y | 3.47 10E7 | 2.56 10E4 | 2.00 10E4 | 2.00 10E7 |
| A | X | 9.38 10E7 | 3.33 10E5 | 9.96 10E5 | 1.42 10E7 |
| A | Y | 1.53 10E8 | 1.01 10E5 | 1.53 10E6 | 7.64 10E4 |
| A | X | 2.46 10E7 | 3.38 10E4 | 9.00 10E4 | 4.56 10E7 |
| A | Y | 1.44 10E7 | 2.06 10E4 | 9.00 10E4 | 4.78 10E7 |
| B | X | 8.00 10E2 | 8.00 10E2 | 8.00 10E2 | 1.30 10E3 |
| B | Y | 8.89 10E6 | 6.80 10E3 | 1.46 10E4 | 4.39 10E4 |
| B | X | 5.56 10E8 | 2.04 10E3 | 2.80 10E6 | 8.99 10E6 |
| B | Y | 4.08 10E5 | 6.43 10E4 | 1.00 10E3 | 7.00 10E6* |
| B | X | 3.18 10E3 | 1.59 10E3 | 1.00 10E3 | 1.06 10E3 |
| B | Y | 5.36 10E5 | 3.22 10E3 | 1.00 10E3 | 7.50 10E5 |
| B | X | 3.20 10E5 | 6.80 10E4 | 1.00 10E3 | 3.05 10E4 |
| B | Y | 2.68 10E4 | 3.35 10E4 | 1.91 10E3 | 1.44 10E3 |
| B | X | 1.83 10E3 | 2.44 10E3 | 1.22 10E3 | 3.06 10E3 |
| B | Y | 5.36 10E5 | 7.49 10E3 | 3.12 10E4 | 4.37 10E4 |
| B | X | 5.63 10E3 | 9.39 10E2 | 9.00 10E2 | 9.00 10E2* |
| B | Y | 1.15 10E5 | 2.19 10E3 | 8.00 10E2 | 4.60 10E4 |
| B | X | 1.31 10E3 | 1.00 10E3 | 1.00 10E3 | 1.31 10E3 |
| B | Y | 1.18 10E4 | 1.31 10E3 | 1.00 10E3 | 6.54 10E4 |
| B | X | 2.68 10E3 | 1.00 10E3 | 1.00 10E3 | 6.71 10E2 |
| B | Y | 5.63 10E5 | 2.64 10E3 | 1.00 10E3 | 9.10 10E4 |
| B | X | 1.66 10E4 | 5.53 10E2 | 1.00 10E3 | 2.21 10E5 |
| B | Y | 1.17 10E7 | 2.74 10E4 | 1.00 10E3 | 2.28 10E5 |
| B | X | 3.14 10E5 | 6.28 10E2 | 1.00 10E3 | 1.26 10E3 |
| B | Y | 1.15 10E7 | 1.10 10E5 | 1.00 10E3 | 7.00 10E6* |
| C | X | 5.43 10E6 | 2.22 10E3 | 1.00 10E4 | 1.11 10E4 |
| C | Y | 5.69 10E7 | 2.00 10E4 | 3.01 10E6 | 5.57 10E4 |

TABLE 8-continued

Series 2
Counts per gram dry weight in treated and untreated
low organic content perlite in a glasshouse.
N.B. Counts are exponents,
i.e. 5.08 10E7 = 5.08 × $10^7$

| Treatment | Type | Bacteria | Spore | Yeast | Moulds |
|---|---|---|---|---|---|
| C | X | 1.38 10E7 | 2.59 10E3 | 1.00 10E4 | 1.00 10E4* |
| C | Y | 1.69 10E8 | 1.75 10E5 | 1.15 10E7 | 6.00 10E7* |
| C | X | 2.07 10E6 | 9.74 10E3 | 1.00 10E4 | 5.93 10E6 |
| C | Y | 1.09 10E6 | 2.16 10E3 | 1.08 10E5 | 4.31 10E5 |
| C | X | 1.52 10E7 | 5.99 10E4 | 1.00 10E4 | 1.16 10E5 |
| C | Y | 3.12 10E7 | 2.48 10E4 | 1.00 10E4 | 5.74 10E4 |
| C | X | 1.00 10E7 | 5.00 10E4 | 1.00 10E4 | 2.08 10E6 |
| C | Y | 2.20 10E7 | 4.77 10E3 | 7.94 10E5 | 1.06 10E5 |
| C | X | 6.00 10E6 | 6.58 10E2 | 1.00 10E4 | 1.00 10E4* |
| C | Y | 1.63 10E7 | 1.24 10E4 | 1.55 10E4 | 3.09 10E4 |
| C | X | 4.96 10E7 | 2.89 10E3 | 1.15 10E4 | 2.31 10E4 |
| C | Y | 5.29 10E7 | 5.71 10E4 | 1.00 10E4 | 6.91 10E5 |
| C | X | 1.62 10E7 | 1.40 10E3 | 1.00 10E4 | 1.00 10E4* |
| C | Y | 1.20 10E7 | 2.08 10E4 | 1.00 10E4 | 4.02 10E6 |
| C | X | 4.25 10E8 | 2.83 10E3 | 1.00 10E4 | 1.00 10E4* |
| C | Y | 6.24 10E7 | 2.11 10E4 | 1.00 10E4 | 6.14 10E6 |
| C | X | 1.41 10E7 | 6.40 10E2 | 1.00 10E4 | 1.28 10E4 |
| C | Y | 1.56 10E7 | 2.51 10E4 | 5.61 10E5 | 1.00 10E4* |

Key:
Treatment:
A = Before application
B = Immediately after application
C = 1 week after application/flushing
Location:
X = Below inlet
Y = Horizontally remote from inlet
= *Inaccurate due to overgrown plates.

Plant growth under simulated commercial conditions following substrate treatment were investigated:

TOMATO PRODUCTION

Procedure

Tomato seed, cv. Shirley, was sown into fine grade perlite, and propagated under standard commercial conditions. Seedlings were pricked out into horticultural grade perlite in 13 cm mesh-based pots. These were maintained in a heated glasshouse until the first flower on the majority of plants was open, at which point they were planted by plunging the pots into the perlite contained in bags, arranged as previously described. Planting was carried out after 45 days.

On the basis of previous trials results application of composition A was at a dilution rate of 1:100 with mains water. This was applied by commercially available irrigation harness as previously described.

Experimental design was modified because of the complexity of the experimental procedure adopted for microbiological assay and the need for re-installation of treated and untreated substrates for the procedures described previously. Plots were of previously used perlite only for crop trials.

Crop yields were recorded over the period 10½ to 12 weeks after plating. Yield was only recorded in terms of gross marketable class I yield irrespective of colour. This was done in order to include green and blotchy red fruit, produced solely as a result of low autumn/early winter light, in the data. Fruit of this type would mature normally for crops grown in spring/summer as is generally the case in the U.K.

Nutrients were applied according to current WSC recommendations.

No evidence of phytotoxic residues were detected in crops grown in perlite previously treated with composition A and subsequently flushed with water. No scorching of leaf margins, as noted in some previous, preliminary trials work occurred, nor were any chlorotic symptoms, typical of low dose phytotoxicity, observed. All foliage was of a uniform dark green colour typically associated with healthy plants.

Early yield of fruit from plots previously treated with product was greater than that from untreated substrates, (Table 9). This trend continued at the second pick but the situation was subsequently reversed. In each case differences between treatments were small. In economic terms early plant establishment and yield is more important than development later in the cropping sequence. These results support the view that composition A can have a beneficial effect on plant establishment in comparison to untreated plots, even in the absence of specific disease organisms.

TABLE 9

Cumulative yield of tomato fruit from plots treated with or without composition A

| Treatment | Yield (kg/plot) Pick No. | | |
|---|---|---|---|
| | 1 | 2 | 3 |
| Treated | 0.29 | 0.77 | 1.53 |
| Untreated | 0.27 | 0.65 | 1.57 |

CUCUMBER PRODUCTION

Procedure

Cucumber seed (cv. Birgit) was surface sown onto moist perlite.

Chitted seeds were transferred to horticultural grade perlite contained in 13 cm mesh-based pots and propagated under standard commercial conditions.

Planting, after 45 days, was by plunging the pots directly into planting holes of the previous crop in perlite. Treatments were of samples previously treated or untreated with composition A.

The crop was trained vertically, and side shoots removed until plants reached the glasshouse eaves height.

Picking commenced 3½ weeks after planting, and continued for seven weeks. Fruit was graded for quality according to EEC regulations. Class I fruit only was graded for weight of individual fruit.

Cucumber plants, which are widely acknowledged as being very sensitive to changes both in aerial and root environments, all established well. No evidence of phytotoxic residues, either as necrosis or chlorosis, was observed. Foliage was all a uniform dark green colour.

Total yield of fruit was better in plots previously treated with composition A (Table 10).

Differences in yield were most marked for early picks, indicating a beneficial effect of product on plant establishment and young plant development.

In terms of fruit grade and quality, treatments were not significantly different. Fruit was predominantly small (250–400 g) with a high proportion of Class II fruit, resulting from reducing light levels over the trial period (Table 11).

TABLE 10

Mean cumulative yield of cucumber fruit, in plots treated with composition A and in untreated controls.

| Treatment | Yield (fruit/plant) Picking Date | | | | |
|---|---|---|---|---|---|
| | 24th Oct | 31st Oct | 7th Nov | 21st Nov | 12th Dec |
| Treated | 0.61 | 1.00 | 1.45 | 1.91 | 3.44 |
| Untreated | 0.50 | 0.80 | 1.39 | 1.89 | 3.38 |

TABLE 11

Comparative quality and numbers of fruit grown in treated and untreated perlite.

| | Mean numbers of fruit/plot | | | | |
|---|---|---|---|---|---|
| | Class I | | Total | | |
| | 250–400 g | 400–500 g | Class I | Class II | Total |
| Treated | 68 | 2 | 70 | 33 | 103 |
| Untreated | 66 | 1 | 67 | 35 | 102 |

EXAMPLE 3

An aqueous concentrate comprising peracetic acid was made by mixing the following ingredients.

| | Percent m/m |
|---|---|
| Acetic acid (80% solution) | 12.8 |
| Hydrogen peroxide (50% solution) | 51.5 |
| 2,6-pyridine dicarboxylic acid | 0.015 |
| Dodecylbenzene sulphonic acid | 1.2 |
| Acetodiphosphonic acid | 2.0 |
| Deionised water | 32.485 |

The composition (composition "B") was mixed, left to stand at 50° C. for 19 hours, cooled to ambient temperature and sampled prior to use to determine the peracetic acid content.

The effect of changes in the concentration of composition B and the effect of increased rate of application and efficacy in two different growing substrates were investigated.

MATERIALS

Corp: Tomato cultivar was MARATHON
Substrates: Perlite (Tilcon Ltd.) Rockwool (Capogro [Pilkington Ltd])

Composition B application rates for each substrate were as follows.

| 1:25 | 1:50 | 1:75 | 1:100 | Control |
|---|---|---|---|---|

Plot size was 16 plants/plot, with three replicates per treatment.

Application method

Bulk tank of diluted composition B was pumped directly via standard irrigation harness to crop plant 'stations'.

Mean application rate was 14.84 dm$^3$ per hour (10.975 dm$^3$).

Substrates were treated to excess run-off, (2.5 dm$^3$/station for rockwool, 5.3 dm$^3$/station for perlite).

The crop was arranged in a statistically randomised layout of three replicates of each treatment.

Crop substrates were sampled for populations of fungi, bacteria and yeasts before, immediately after application of composition B and after subsequent rinsing.

No evidence of phytotoxicity was noted in plants established by normal commercial procedures into Crop substrates treated with composition B and subsequently flushed with clean water.

With regard to efficacy, composition B's ability to reduce populations of fungi, bacteria and yeasts was again demonstrated. Results are summarised in Tables 12 to 17.

In the case of Rockwool substrates application of composition B at 1:50 or above to markedly reduce the population of fungi, bacteria and yeasts. In the case of perlite a similar effect was achieved at a lower concentration;-1:75. It is a feature of this technique that recolonisation of the material by naturally occurring organisms takes place within a short time. This feature of low persistence/low toxicity is compatible with the theoretical reintroduction of beneficial organisms in an integrated biological control programme.

TABLE 12

Rockwool Bacterial Counts

Counts per gram dry weight

| | Before disinfection | After disinfection | After washing |
|---|---|---|---|
| Control (water) | $4.70 \times 10^8$ | $6.19 \times 10^7$ | $4.90 \times 10^8$ |
| | $4.32 \times 10^6$ | $9.23 \times 10^8$ | $8.30 \times 10^8$ |
| | $2.88 \times 10^7$ | $1.47 \times 10^9$ | $1.98 \times 10^8$ |
| 1:100 dilution | $1.35 \times 10^9$ | $5.76 \times 10^5$ | $1.30 \times 10^9$ |
| | $7.47 \times 10^7$ | $1.53 \times 10^8$ | $2.15 \times 10^9$ |
| | $1.63 \times 10^7$ | $9.36 \times 10^6$ | $4.20 \times 10^7$ |
| 1:75 dilution | $1.22 \times 10^7$ | $1.81 \times 10^8$ | $2.68 \times 10^7$ |
| | $2.70 \times 10^5$ | $1.42 \times 10^8$ | $1.66 \times 10^9$ |
| | $3.20 \times 10^8$ | $3.93 \times 10^8$ | $1.96 \times 10^4$ |
| 1:50 dilution | $1.72 \times 10^8$ | $1.78 \times 10^4$ | $1.84 \times 10^9$ |
| | $3.24 \times 10^8$ | $<2.70 \times 10^2$ | $2.60 \times 10^9$ |
| | $1.22 \times 10^6$ | $<2.70 \times 10^2$ | $1.23 \times 10^4$ |
| 1:25 dilution | $7.57 \times 10^6$ | $<2.70 \times 10^2$ | $1.49 \times 10^9$ |
| | $5.27 \times 10^6$ | $3.57 \times 10^6$ | $1.39 \times 10^7$ |
| | $2.83 \times 10^8$ | $<2.70 \times 10^2$ | $3.32 \times 10^6$ |

TABLE 13

Rockwool Yeast Counts

Counts per gram dry weight

| | Before disinfection | After disinfection | After washing |
|---|---|---|---|
| Control (water) | $2.83 \times 10^6$ | $3.43 \times 10^3$ | $2.24 \times 10^6$ |
| | $2.70 \times 10^4$ | $3.93 \times 10^3$ | $4.03 \times 10^4$ |
| | $2.30 \times 10^4$ | $3.70 \times 10^5$ | $2.26 \times 10^4$ |
| 1:100 dilution | $<2.70 \times 10^3$ | $<2.70 \times 10^2$ | $<2.70 \times 10^2$ |
| | $1.05 \times 10^4$ | $6.40 \times 10^3$ | $1.20 \times 10^5$ |
| | $5.44 \times 10^4$ | $<2.70 \times 10^2$ | $<2.70 \times 10^2$ |
| 1:75 dilution | $5.73 \times 10^3$ | $6.27 \times 10^5$ | $6.35 \times 10^5$ |
| | $<2.70 \times 10^3$ | $4.16 \times 10^3$ | $5.42 \times 10^4$ |
| | $<2.70 \times 10^3$ | $<2.70 \times 10^2$ | $<2.70 \times 10^2$ |
| 1:50 dilution | $<2.70 \times 10^3$ | $<2.70 \times 10^2$ | $4.36 \times 10^5$ |
| | $<2.70 \times 10^3$ | $<2.70 \times 10^2$ | $<2.70 \times 10^2$ |
| | $4.05 \times 10^3$ | $<2.70 \times 10^2$ | $<2.70 \times 10^2$ |
| 1:25 dilution | $<2.70 \times 10^3$ | $<2.70 \times 10^2$ | $<2.70 \times 10^2$ |
| | $9.46 \times 10^5$ | $2.69 \times 10^4$ | $<2.70 \times 10^2$ |
| | $<2.70 \times 10^3$ | $<2.70 \times 10^2$ | $<2.70 \times 10^2$ |

TABLE 14

Rockwool Mould Counts

Counts per gram dry weight

| | Before disinfection | After disinfection | After washing |
|---|---|---|---|
| Control (water) | $2.53 \times 10^6$ | $1.49 \times 10^3$ | $9.47 \times 10^6$ |
| | $<2.70 \times 10^3$ | $6.05 \times 10^5$ | $2.78 \times 10^5$ |
| | $1.01 \times 10^5$ | $5.86 \times 10^5$ | $2.90 \times 10^5$ |
| 1:100 dilution | $1.51 \times 10^7$ | $1.46 \times 10^5$ | $6.05 \times 10^4$ |
| | $4.21 \times 10^5$ | $5.22 \times 10^5$ | $6.84 \times 10^6$ |
| | $1.75 \times 10^5$ | $7.52 \times 10^3$ | $3.80 \times 10^4$ |
| 1:75 dilution | $3.64 \times 10^5$ | $7.09 \times 10^5$ | $7.47 \times 10^6$ |
| | $1.62 \times 10^4$ | $1.52 \times 10^5$ | $4.69 \times 10^6$ |
| | $5.59 \times 10^5$ | $1.89 \times 10^6$ | $<2.70 \times 10^2$ |
| 1:50 dilution | $1.06 \times 10^6$ | $2.27 \times 10^3$ | $6.28 \times 10^6$ |
| | $1.54 \times 10^6$ | $<2.70 \times 10^2$ | $2.55 \times 10^7$ |
| | $1.49 \times 10^4$ | $<2.70 \times 10^2$ | $<2.70 \times 10^2$ |
| 1:25 dilution | $1.22 \times 10^6$ | $3.08 \times 10^3$ | $>2.00 \times 10^7$ |
| | $5.14 \times 10^6$ | $3.11 \times 10^4$ | $>2.00 \times 10^5$ |
| | $2.62 \times 10^6$ | $<2.70 \times 10^2$ | $<2.70 \times 10^2$ |

TABLE 15

Perlite Bacterial Counts

Counts per gram dry weight

| | Before disinfection | After disinfection | After washing |
|---|---|---|---|
| Control (water) | $1.33 \times 10^8$ | $9.67 \times 10^7$ | $2.18 \times 10^8$ |
| | $9.71 \times 10^7$ | $1.05 \times 10^8$ | $8.63 \times 10^6$ |
| | $3.44 \times 10^7$ | $7.02 \times 10^5$ | $1.85 \times 10^5$ |
| 1:100 dilution | $1.70 \times 10^7$ | $2.68 \times 10^6$ | $3.01 \times 10^6$ |
| | $4.60 \times 10^7$ | $<2.70 \times 10^2$ | $1.83 \times 10^6$ |
| | $1.10 \times 10^7$ | $3.36 \times 10^6$ | $4.20 \times 10^7$ |
| 1:75 dilution | $1.22 \times 10^7$ | $<2.70 \times 10^2$ | $1.58 \times 10^6$ |
| | $1.11 \times 10^8$ | $<2.70 \times 10^2$ | $2.93 \times 10^6$ |
| | $1.80 \times 10^7$ | $<2.70 \times 10^2$ | $1.06 \times 10^4$ |
| 1:50 dilution | $1.50 \times 10^8$ | $<2.70 \times 10^2$ | $1.00 \times 10^7$ |
| | $8.53 \times 10^6$ | $<2.70 \times 10^2$ | $1.22 \times 10^8$ |
| | $4.97 \times 10^6$ | $2.84 \times 10^3$ | $<2.70 \times 10^2$ |
| 1:25 dilution | $3.20 \times 10^7$ | $<2.70 \times 10^2$ | $9.91 \times 10^7$ |
| | $1.40 \times 10^8$ | $4.05 \times 10^2$ | $4.55 \times 10^8$ |
| | $2.32 \times 10^6$ | $<2.70 \times 10^2$ | $6.64 \times 10^4$ |

TABLE 16

Perlite Yeast Counts

Counts per gram dry weight

| | Before disinfection | After disinfection | After washing |
|---|---|---|---|
| Control (water) | $2.22 \times 10^5$ | $<2.70 \times 10^2$ | $2.24 \times 10^5$ |
| | $5.74 \times 10^4$ | $4.20 \times 10^4$ | $<2.70 \times 10^2$ |
| | $2.15 \times 10^4$ | $<2.70 \times 10^2$ | $3.12 \times 10^3$ |
| 1:100 dilution | $1.97 \times 10^5$ | $<2.70 \times 10^2$ | $<2.70 \times 10^2$ |
| | $6.43 \times 10^4$ | $<2.70 \times 10^2$ | $9.94 \times 10^4$ |
| | $3.21 \times 10^5$ | $4.11 \times 10^4$ | $4.48 \times 10^4$ |
| 1:75 dilution | $1.36 \times 10^4$ | $<2.70 \times 10^2$ | $<2.70 \times 10^2$ |
| | $4.30 \times 10^4$ | $<2.70 \times 10^2$ | $<2.70 \times 10^2$ |
| | $1.37 \times 10^6$ | $<2.70 \times 10^2$ | $<2.70 \times 10^2$ |
| 1:50 dilution | $<2.70 \times 10^3$ | $<2.70 \times 10^2$ | $<2.70 \times 10^2$ |
| | $<2.70 \times 10^3$ | $<2.70 \times 10^2$ | $<2.70 \times 10^2$ |
| | $<2.70 \times 10^3$ | $3.35 \times 10^3$ | $<2.70 \times 10^2$ |
| 1:25 dilution | $1.38 \times 10^5$ | $<2.70 \times 10^2$ | $<2.70 \times 10^2$ |
| | $3.28 \times 10^4$ | $<2.70 \times 10^2$ | $<2.70 \times 10^2$ |
| | $<2.70 \times 10^3$ | $<2.70 \times 10^2$ | $<2.70 \times 10^2$ |

TABLE 17

Perlite Mould Counts

Counts per gram dry weight

| | Before disinfection | After disinfection | After washing |
|---|---|---|---|
| Control (water) | $2.57 \times 10^5$ | $<2.70 \times 10^2$ | $5.59 \times 10^5$ |
| | $2.68 \times 10^4$ | $5.08 \times 10^4$ | $1.36 \times 10^5$ |
| | $2.23 \times 10^5$ | $7.34 \times 10^3$ | $7.28 \times 10^5$ |
| 1:100 dilution | $>2.00 \times 10^7$ | $1.82 \times 10^6$ | $1.72 \times 10^6$ |
| | $1.37 \times 10^5$ | $<2.70 \times 10^2$ | $3.05 \times 10^4$ |
| | $>2.00 \times 10^7$ | $7.80 \times 10^4$ | $2.56 \times 10^5$ |
| 1:75 dilution | $5.45 \times 10^4$ | $<2.70 \times 10^2$ | $>2.00 \times 10^7$ |
| | $6.62 \times 10^5$ | $<2.70 \times 10^2$ | $3.86 \times 10^5$ |
| | $1.68 \times 10^5$ | $<2.70 \times 10^2$ | $4.89 \times 10^3$ |
| 1:50 dilution | $>2.00 \times 10^7$ | $<2.70 \times 10^2$ | $4.08 \times 10^6$ |
| | $>2.00 \times 10^5$ | $3.30 \times 10^3$ | $<2.70 \times 10^2$ |
| | $>2.00 \times 10^5$ | $<2.70 \times 10^2$ | $<2.70 \times 10^2$ |
| 1:25 dilution | $2.29 \times 10^6$ | $<2.70 \times 10^2$ | $2.33 \times 10^3$ |
| | $7.55 \times 10^4$ | $<2.70 \times 10^2$ | $1.26 \times 10^7$ |
| | $<2.70 \times 10^3$ | $<2.70 \times 10^2$ | $<2.70 \times 10^2$ |

We claim:

1. In a method of hydroponic crop production wherein plants are grown in a hydroponic system having a hydroponic substrate to support the plants and a nutrient liquid-supply means including an irrigation system, to supply nutrient liquid to said hydroponic substrate;

the improvement comprising
reducing but not eliminating microbial population in said hydroponic substrate and/or liquid-supply means of said hydroponic system which has been infected with a microbial population as a result of a crop-production cycle and prior to a subsequent crop production cycle by treating said hydroponic substrate and/or liquid supply means with a dilute aqueous solution containing at least one peracid having a percarboxy group, in an amount sufficient substantially to reduce but not eliminate the microbial population.

2. The method according to claim 1 wherein the dilute aqueous solution contains hydrogen peroxide and a percarboxylic acid.

3. The method according to claim 2, wherein the peracid is peracetic or perpropionic acid.

4. The method according to any one of claims 1 to 2, wherein the hydroponic substrate contains less than 5% by volume of organic matter at the time of the said treatment.

5. The method according to any one of claims 1 to 3, wherein the hydroponic substrate contains less than 2% by volume of organic matter at the time of the said treatment.

6. The method according to any one of claims 1 to 3, wherein the hydroponic substrate contains less than 0.5% by volume of organic matter at the time of the said treatment.

7. The method according to any one of claims 1 to 3, wherein the treatment solution contains a stabilizer for percarboxylic acids.

8. The method according to any one of claims 1 to 3, wherein the peracid of the treatment solution is generated by the reaction of hydrogen peroxide with the corresponding acid or acid anhydride.

9. The method according to any one of claims 1 to 3, wherein the treatment solution is prepared by dilution of a more concentrated solution of the peracid.

10. The method according to any one of claims 1 to 3, wherein the application ratio of treatment solution to hydroponic substrate is from 0.1:1 to 5.0:1 by volume.

11. The method according to any one of claims 1 to 3, wherein the treatment solution is free from significant quantities of dissolved salts.

12. The method according to claim 11, wherein the treatment solution contains wetting agent.

13. The method according to claim 12, wherein the wetting agent has bactericidal activity.

14. The method according to any one of claims 1 to 3, wherein the treatment solution contains a wetting agent.

15. The method according to claim 14, wherein the wetting agent has bactericidal activity.

16. The method according to claim 15 wherein the wetting agent is an alkylaryl sulphonic acid having from 6 to 18 carbon atoms in the alkyl substituent of the molecule.

17. The method according to claim 16, wherein the wetting agent is dodecyl benzene sulphonic acid.

18. The method according to any one of claims 1 to 3, wherein the concentration of peracid in the treatment solution is from 0.001 to 0.05 mol dm$^3$.

19. The method according to claim 18, wherein the concentration of peracid in the treatment solution is from 0.0025 to 0.02 mol dm$^3$.

20. The method according to claim 19, wherein the concentration of peracid in the treatment solution is from 0.005 to 0.01 mol dm$^3$.

21. The method according to any one of claims 1 to 3, wherein the ratio of hydrogen peroxide to peracid in the treatment solution is in the range 2:1 to 10:1 by weight.

22. The method according to claim 21, wherein the ratio is in the range 4:1 to 7:1.

23. The method according to claim 22, wherein the application ratio is from 0.5:1 to 1.0:1 volume.

24. The method according to any one of claims 1 to 3, wherein the treatment solution is supplied to the substrate through the same irrigation system as is used for supply of liquid nutrients to the plants during the growing cycle.

25. The method according to claim 24, wherein the application ratio is from 0.66:1 to 0.83:1 by volume.

* * * * *